(12) United States Patent
Ambasz

(10) Patent No.: US 6,478,379 B1
(45) Date of Patent: Nov. 12, 2002

(54) CHAIR

(75) Inventor: Emilio Ambasz, Buenos Aires (AR)

(73) Assignee: Center For Design Research and Development N.V., Curacao (NL)

( * ) Notice: Subject to any disclaimer, the term of this patent is extended or adjusted under 35 U.S.C. 154(b) by 185 days.

(21) Appl. No.: 09/589,332

(22) Filed: Jun. 7, 2000

(51) Int. Cl.[7] ................................................ A47C 7/40
(52) U.S. Cl. .............................. 297/354.11; 297/284.3; 297/291
(58) Field of Search ........................... 297/284.3, 284.4, 297/284.11, 291, 292, 293, 299, 353, 354.1, 354.11

(56) References Cited

U.S. PATENT DOCUMENTS

| 590,045 A | 9/1897 | Mauchain |
| 1,720,794 A | 7/1929 | Kusterle |
| 2,098,456 A | 11/1937 | Leader et al. |
| 3,540,777 A | 11/1970 | Beaumont |
| 4,768,833 A | 9/1988 | Virtue |
| 5,100,201 A | 3/1992 | Becker, III et al. |
| 5,120,109 A | 6/1992 | Rangoni |
| 5,447,356 A | 9/1995 | Snijders |
| 5,597,203 A | 1/1997 | Hubbard |

FOREIGN PATENT DOCUMENTS

| GB | 11264 | * 6/1846 | ............... 297/284.4 |
| GB | 680854 | * 10/1952 | ................. 297/291 |

* cited by examiner

Primary Examiner—Peter R. Brown
(74) Attorney, Agent, or Firm—Baker Botts LLP

(57) ABSTRACT

A chair has a pair of spaced-apart back support mounting members, a lower back support adapted to support the lower portion of the back of a person seated on the chair and mounted on the back support mounting members for pivotal movement about a pivot axis located at substantially the vertical centerline of the lower back support, and an upper back support adapted to support the upper portion of the back of a person seated on the chair and mounted on the back support mounting members for pivotal movement about a pivot axis located at substantially the vertical centerline of the upper back support.

19 Claims, 16 Drawing Sheets

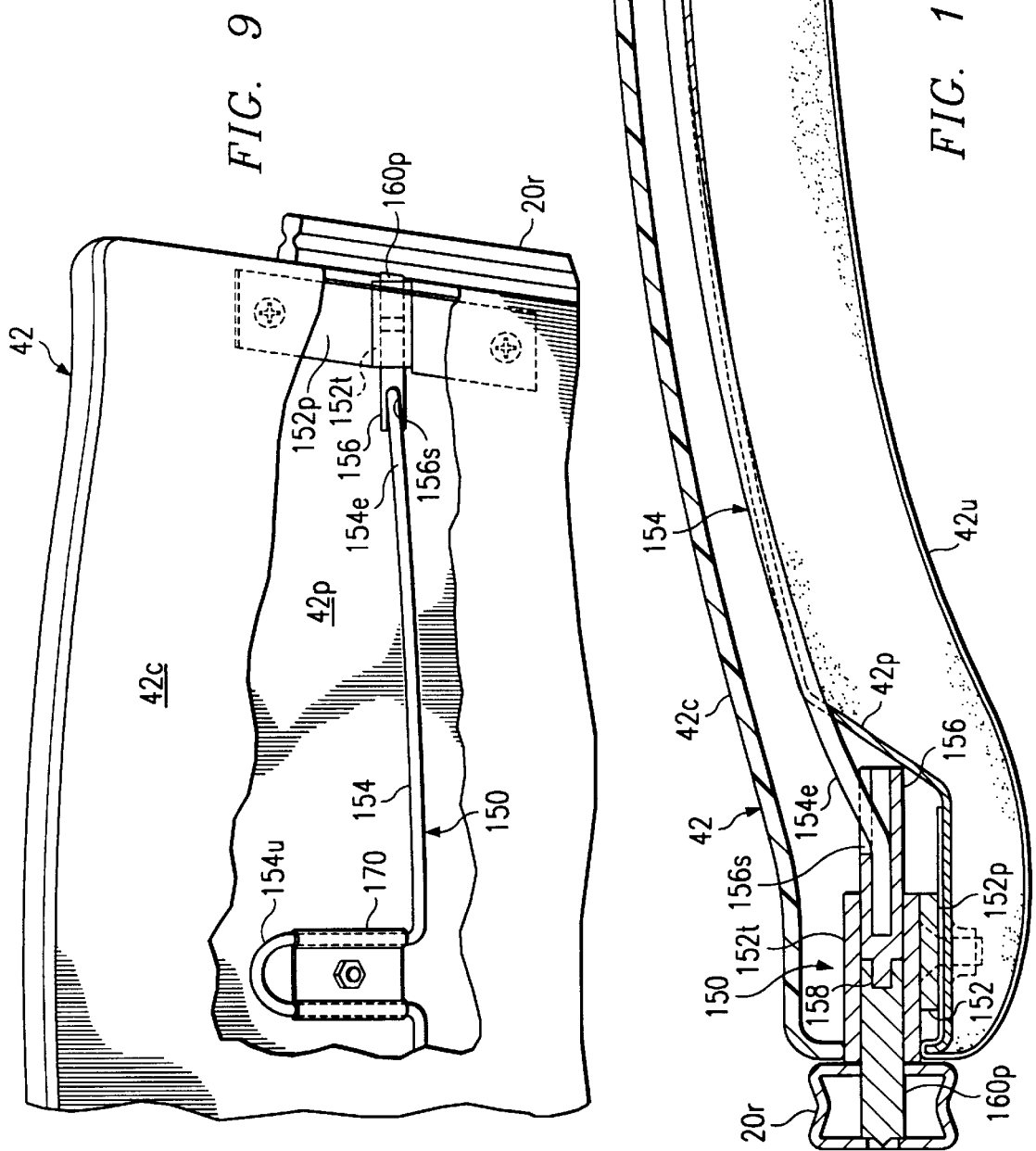

CHAIR

BACKGROUND OF THE INVENTION

The rapid development of the "new economy" in recent years has required office workers at all levels to spend ever-increasing amounts of time working at computers. No longer is the use of a keyboard the province of a typist/secretary or word processor operator. Managers frequently communicate by E-mail and access company data and websites for information required for carrying out their duties. Product design and development, purchasing, marketing, production, shipping, and virtually all other activities in industry and commerce are done with the aid of computers. Professionals likewise use computers for obtaining information, communicating, and for creating documents and computer data files.

Sitting upright in a somewhat forward-leaning position to work at a keyboard places considerable strain on the back and is highly fatiguing. Minimizing strain and fatigue requires a chair that provides excellent support for the user's back, not only in a working position but a relaxed position. In that regard, it is also important for reducing strain for persons working at a computer or over papers on a desk to be able to change their positions frequently and to be able to lean back to a rest position from time to time.

Currently available office chairs allow various adjustments that improve seating comfort in working and relaxed postures. For example, seat mounts that allow the entire chair to tilt backward and forward are very common. Some office chairs have back supports that tilt backward relative to the seat bottom or seat bottoms that slide forward and backward relative to the back support, or both. Most typists chairs have a back support that pivots so as to self-adjust to the sitting posture of the user. Office chairs usually have a support column that permits adjustment of the height of the entire seat (bottom and backrest) above the floor. Many typists chairs also provide for adjustment of the height of the back support relative to the seat.

A need that has not, to the present inventor's knowledge, been adequately met by previously known and/or available office chairs is a chair back that provides good support for the entire anatomical back of a user from the sacrum to the shoulders over a range of seating postures. On the one hand, office chairs designed for use by typists have a back support that self-adjusts about a horizontal pivot axis but is relatively small so that it supports only the lower back. Managerial and executive chairs, on the other hand, have large back supports that are of fixed shapes. The anatomical back assumes widely different vertical curvatures, depending on the seating posture. Chair back supports of fixed shapes provide good support in only one seating posture.

SUMMARY OF THE INVENTION

One object of the present invention is to provide an office chair that provides optimal support of the entire back of a user in a wide range of sitting postures. Another object is to provide an office chair of relatively simple construction that permits adjustments of the configurations of the back support and the seat bottom to suit ideally users of all heights. It is also desired to make a chair that meets the foregoing objects attractive in appearance.

The foregoing objects are attained, in accordance with the present invention, by a chair that has a pair of spaced-apart back support mounting members, a lower back support adapted to support the lower portion of the back of a person seated on the chair and mounted on the back support mounting members for pivotal movement about a pivot axis located at substantially the vertical centerline of the lower back support, and an upper back support adapted to support the upper portion of the back of a person seated on the chair and mounted on the back support mounting members for pivotal movement about a pivot axis located at substantially the vertical centerline of the upper back support.

The two back support members of the chair of the present invention provide support of a user's back throughout the region from the sacrum to just above the shoulder blades, which relieves strain on the user's back in all sitting postures and also considerably improves the comfort of the chair in all sitting postures, especially in a leaning back posture. The pivoting of the two back supports independently permits each back support to self-adjust to the curvature in the vertical direction of the user's back, which varies considerably over a range of sitting postures. Pressure loads transferred from back supports to the user's back are, by virtue of the pivoting of both back supports, relatively evenly distributed over the user's back.

The lower back support and upper back support are, preferably, mounted on the back support mounting members by resilient mount units that bias the back supports to a predetermined position. The principal function of the resilient mounting of the two back supports is to keep both back supports in a neutral position when the chair is unoccupied so that it looks better and also so that when someone first sits down, the back supports are in proper position to encounter the user's back with relatively even pressure rather than being far out of position and presenting edges of the supports to the user's back. The spring force acting on each back support should, however, be kept low so that there is little effect on the pressure applied to the user's back when the back supports pivot against the resilient bias—i.e., so that a substantially uniform pressure is applied by each back support to the portion of the user's back engaged by the back support.

Each of the resilient mount units may include an elastomeric body affixed to and interposed functionally between the back support and the back support mounting member. Resilient mount units based on elastomeric members, which are known per se and are commercially available, are quiet in operation, relatively inexpensive, small and compact in size, and easy to install. Various mechanical spring systems can also be used.

In preferred embodiments, the back support mounting members are located laterally abreast of the back supports. That relative disposition of the back supports and the back support mounting members has structural and manufacturing advantages. For example, the back supports may be made large in size, both in height and width; by supporting each of them at each side edge at a single pivot point, torsion loads at the mounting points are not a factor in the design. Each back support, preferably, includes a structural pan for maintaining the shape of the back support under load and for transmitting loads laterally outwardly to the back support mounting members and upholstered padding carried by the pan.

Each of the back supports is, in preferred embodiments, generally rectangular, and the side edges of each of the back supports are closely adjacent the back support mounting members. That configuration provides wide back supports, which distribute the loads applied to the user's back over a large area transversely and for any given total load reduce the pressure on the user's back. Similarly, the upper edge of the lower back support is closely adjacent the lower edge of the upper back support. In addition to keeping the back supports large in area for reduced pressure, the lack of a gap between the two back supports improves the comfort by maintaining continuity of support in the vertical direction.

It is desirable that each of the lower back support and the upper back support be transversely curved and present a transversely concave front surface that corresponds in shape generally to the transverse curvature of the anatomical back of a person. Also, the lower back support is vertically curved and presents a vertically curved convex surface that corresponds in shape generally to the vertical curvature of the lower portion of the anatomical back of a person in the region of the small of the back at the waist.

The chair back structure described above is, of course, mounted on a base having a seat mount supporting a seat bottom. The chair back structure is, preferably, mounted on a back support bracket associated with the seat mount. The back support mounting members are, in preferred embodiments, joined by a transverse framework that is supported by the back support bracket for adjustment of the height of the back support mounting members.

According to another aspect of the present invention, a chair according to the present invention has a seat bottom unit having a body part and a front edge part, the rear edge of the front edge part being coupled to the front edge of the body part for downward articulation of the front edge part from a resiliently restrained upward position. The downwardly tilting front part of the seat bottom allows the front part of the seat to tilt down in response to pressure from the undersides of the lower parts of the user's thighs, thus relieving pressure on them. The seat bottom should be mounted on the seat mount for adjustment forwardly and rearwardly relative to the seat mount so that the chair can be adjusted to suit ideally the height of the user.

In a particularly advantageous construction of the resilient mount units, a first support plate is affixed to one side of the elastomeric member and to the structural pan. A second support plate is affixed to the other side of the elastomeric member. A mounting bracket is affixed to the back support mounting member, and a screw affixes the mounting bracket to the second support plate. The structural pan includes a cavity receiving the first support plate and a portion of the elastomeric member. Each back support mounting member is a tubular member having side walls, and the mounting bracket includes a mounting post that passes through a hole in one side wall of the back support mounting members and is joined to the opposite side wall of the back support mounting members by a weldment at a weld site that includes a hole in the opposite side wall. One advantage of the foregoing construction is that the mounting bracket is very strongly joined to the back support mounting member by passing through a hole in one wall and being joined to the opposite wall by welding at a weld site formed by a hole in the opposite wall. The hole and the weld form two attachment points for the mounting post to the back support mounting member. If desirable or necessary for torsional strength about the pivot axis, both support points can be welded. Another advantage is that the resilient mount can be virtually completely concealed for good appearance of the chair. Furthermore, assembly of each back support to the back support mounting members is facilitated by having a single screw for attaching the bracket of the resilient mount unit.

DESCRIPTION OF THE DRAWINGS

For a more complete understanding of the present invention, and the advantages thereof, reference may be made to the following written description of an exemplary embodiment, taken in conjunction with the accompanying drawings, which show the following views of the embodiment:

FIG. 9—a partial rear elevational view with a portion broken away and showing the modified pivot mount of FIG. 8;

FIG. 10—a partial top cross-sectional view, taken along the lines 10—10 of FIG. 8;

DESCRIPTION OF THE EMBODIMENT

Figure 1:
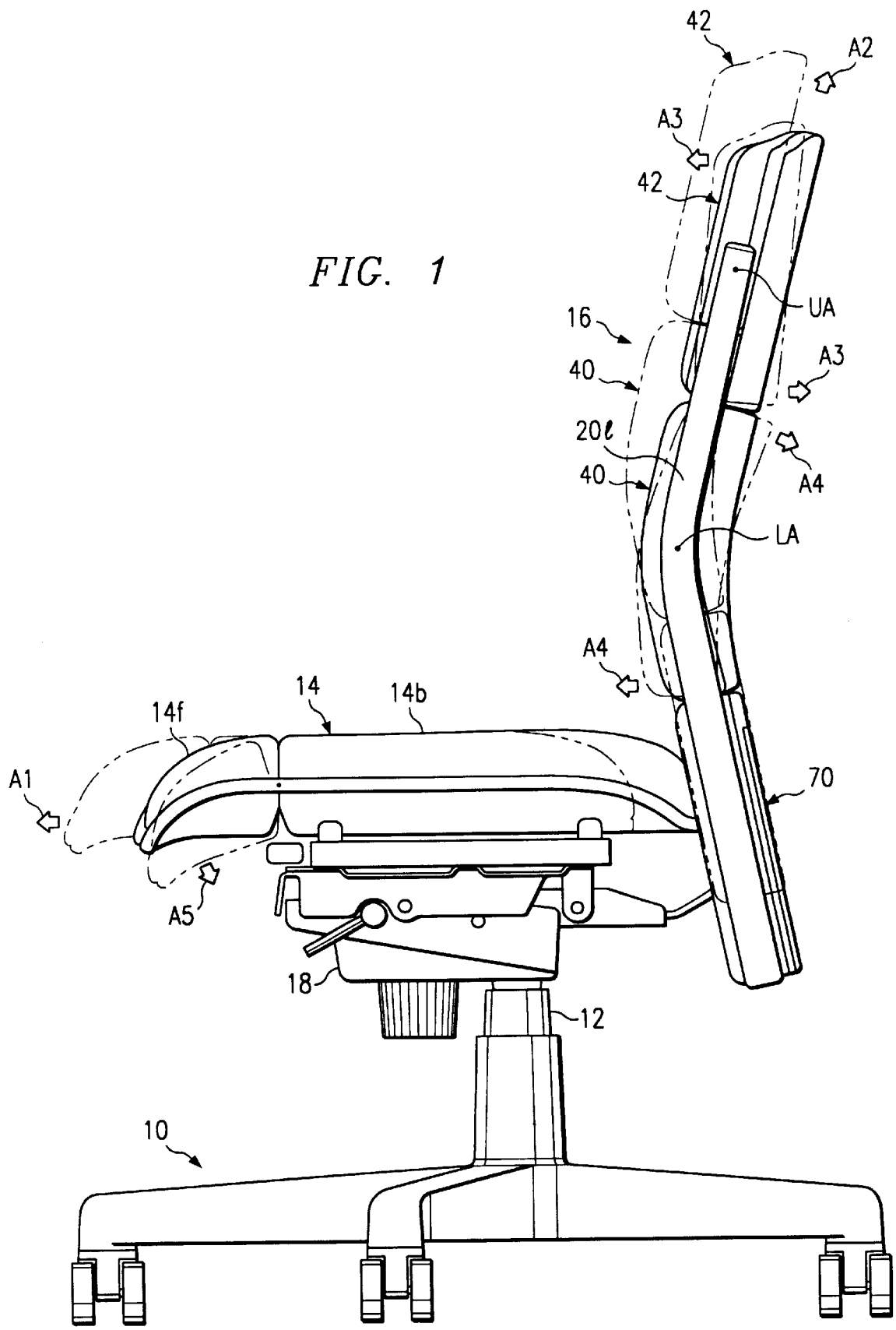
FIG. 1—a side elevational view.

The embodiment has a five-legged caster base 10, a gas spring column 12, which is affixed to the base and permits adjustment of the height of the entire chair seat unit (seat bottom assembly 14 and seat back assembly 16), and a seat-mounting mechanism 18 mounted on the column, which permits the entire seat unit to tilt forward and backward from an upright position and to be locked in the upright or forward tilted position. The seat-mounting mechanism also allows the position of the seat bottom 14 to be adjusted forward and backward, as shown by the small arrow A1, and locked in the desired position. The components described in this paragraph are well-known and available commercially in various specific designs from numerous vendors of parts for office seating. The base for a chair embodying the present invention need not include all of the features described in this paragraph.

Figure 5:
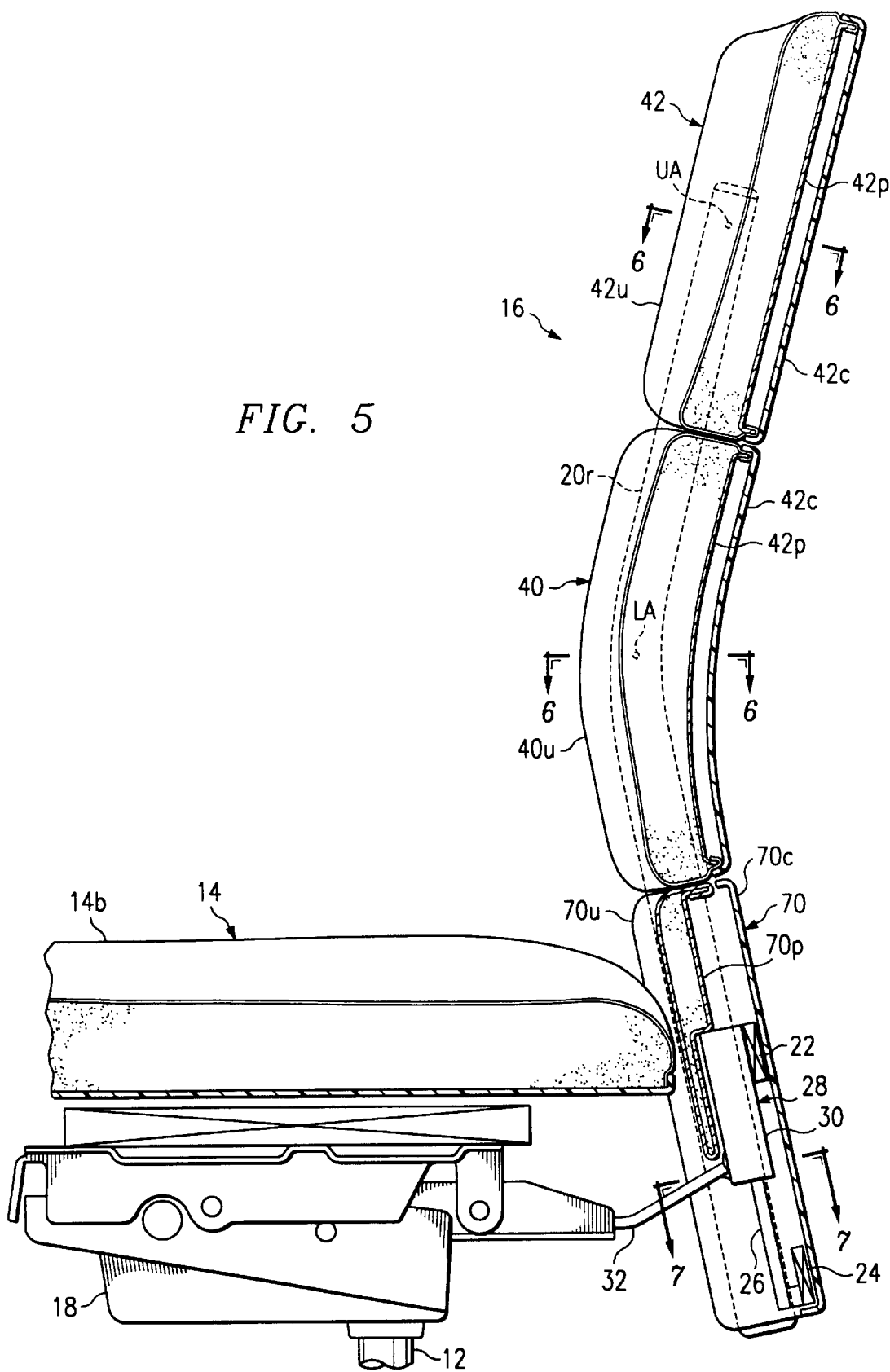
FIG. 5—a partial, generally schematic side cross-sectional view.
Figure 7:
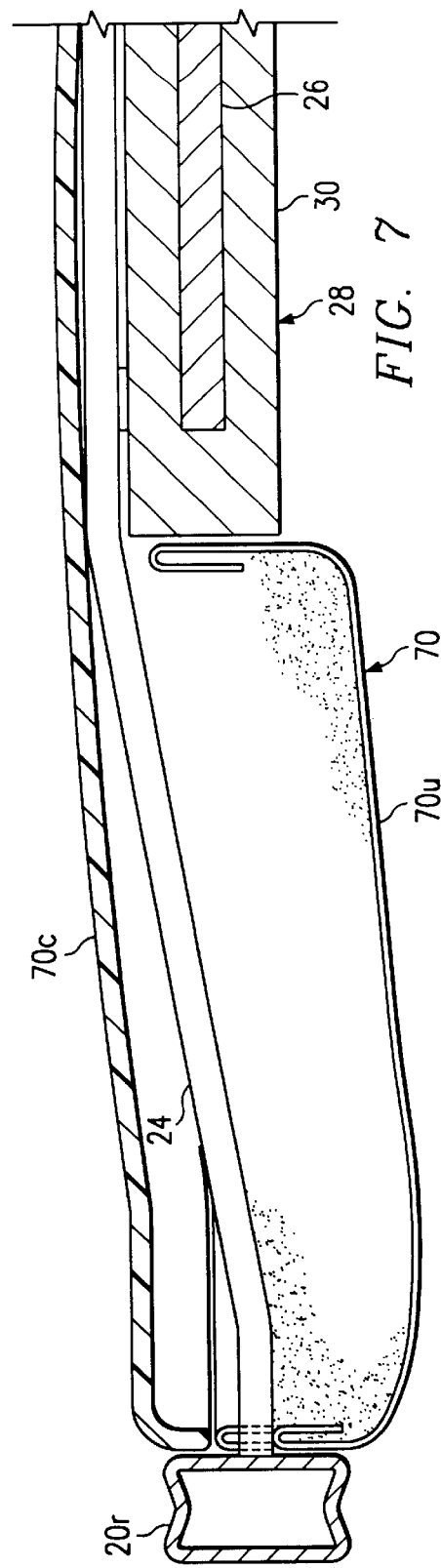
FIG. 7—a partial top cross-sectional view, taken along the lines 7—7 of FIG. 5.

The seat back assembly 16 includes right and left seat back support mounting members 20r and 20l, which are joined to each other near their lower ends by a pair of structural cross-members 22 and 24 (see FIGS. 5 and 7). The cross-members 22 and 24 are affixed to a plate 26 that is part of a seat back height-adjusting unit 28 that is located in the center and to the rear of the seat-mounting mechanism 18 and permits the height of the seat back assembly 16 to be adjusted, as indicated by the arrow A2 and the phantom lines in FIG. 1, and locked in a desired position. The other component 30 (shown schematically in FIGS. 5 and 7 as a box-like part) of the height-adjusting unit is affixed to a back-mounting bracket 32 that is affixed to the seatmounting mechanism 18. Height-adjusting units 28 suitable for use in a chair according to the present invention are well-known and available commercially from various sources.

Figure 2:
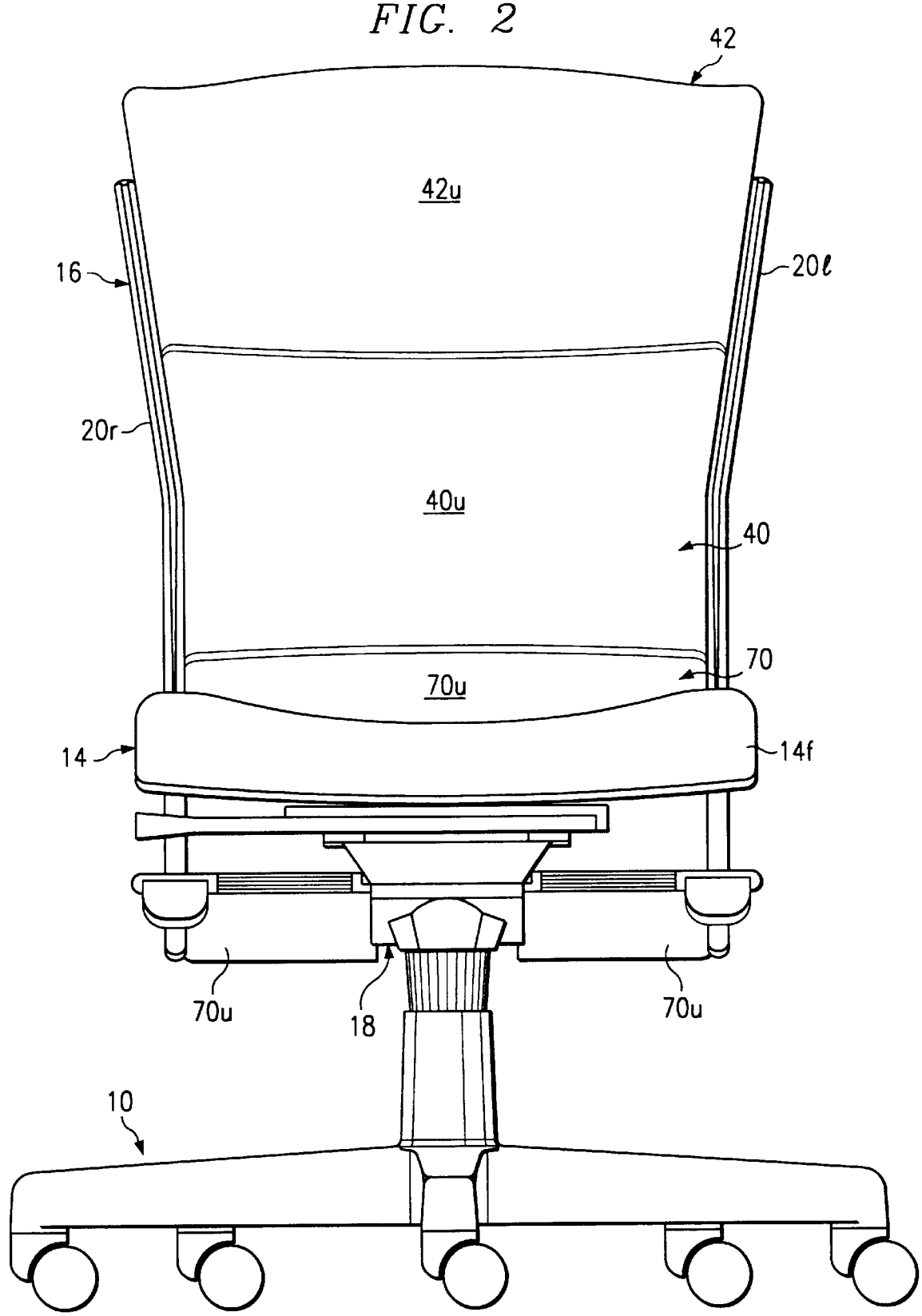
FIG. 2—a front elevational view.

The back support mounting members 20r and 20l are steel tubes that are bent to be bowed in lateral profile (FIG. 1) and also to slope outwardly in an upward direction from points at about waist level in front plan (FIG. 2). A lower back support 40 is mounted on the back support mounting members 20r and 20l for pivotal movement, as indicated by the arrows A3 and the phantom lines in FIG. 1, about a transverse horizontal axis LA located substantially at the vertical centerline of the lower back support 40. An upper back support 42 is mounted on the back support mounting members 20r and 20l for pivotal movement, as indicated by the arrows A4 and the phantom lines in FIG. 1, about a transverse horizontal axis UA located substantially at the vertical centerline of the upper back support 42. Each back support 40 and 42 includes a structural pan 40p, 42p, which may be stamped from metal sheet or molded from a plastic, an upholstered pad 40u, 42u, and a molded plastic rear cover 40c, 42c. The back supports 40 and 42 are generally rectangular in front plan (FIG. 2) and have their side edges located closely adjacent the back support mounting members 20r and 20l, which are located abreast of the back supports. The upper edge of the lower back support 40 lies closely adjacent the lower edge of the upper back support 42. The concepts here are to maximize the sizes of the two back supports for good support of the chair occupant with low pressure applied to the occupant's back for any given load and to avoid discontinuities in the vertical direction. The two back supports are also contoured both horizontally and vertically to present forward surfaces that match generally the anatomical shape of the human back both vertically and horizontally.

Figure 6:
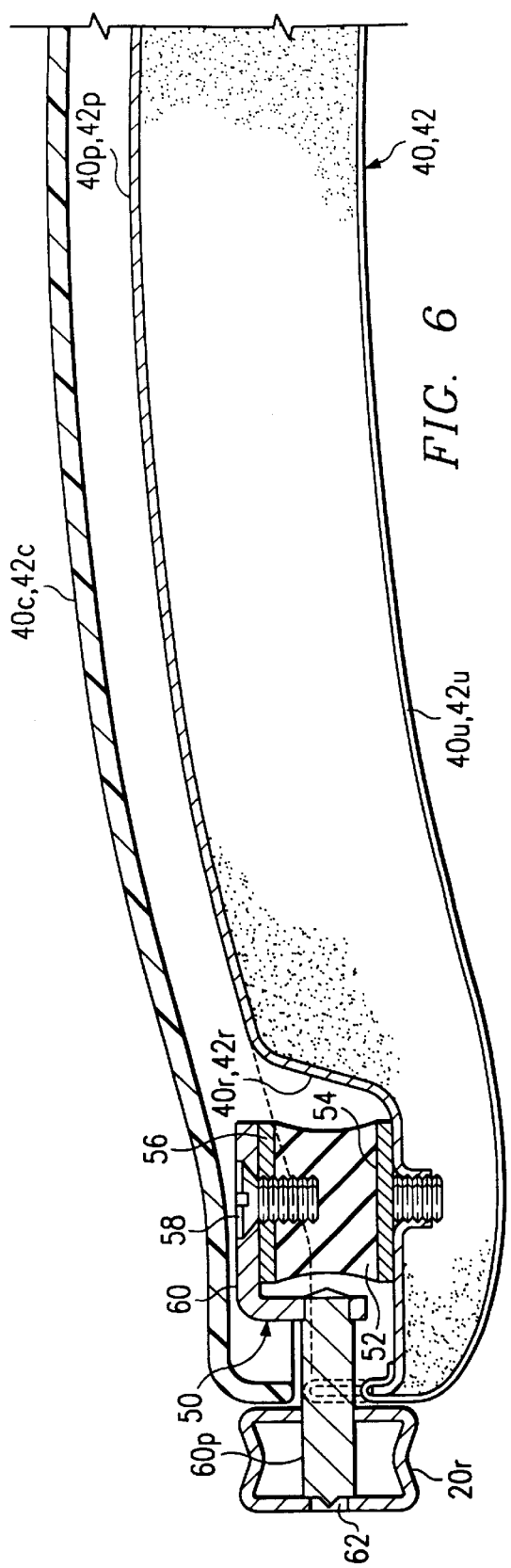
FIG. 6—a partial top cross-sectional view, taken along the lines 6—6 of FIG. 5.

The upper back support 42 and lower back support 40 are mounted on the left and right back support mounting members 20r and 20ls by identical resilient mount units 50, one on each side. Referring to FIG. 6, each resilient mount unit 50 is affixed to the structural pan 40p, 42p of the back support and to the back support mounting member 20r, 20l and includes an elastomeric member 52, a first support plate 54 affixed to one side of the elastomeric member and to the structural pan, and a second support plate 56 affixed to the other side of the elastomeric member. A screw 58 affixes a mounting bracket 60 to the second support plate 56. The structural pan 40p, 42p includes a recess cavity 40r, 42r that accepts the first support plate and a portion of the elastomeric member. The mounting bracket 60 includes a mounting post 60p that passes through a hole in the near side wall of the back support mounting member 20r, 20l and is joined to the opposite side wall of the back support mounting member by a weldment 62 at a weld site that includes a hole in the opposite side wall.

The pan 40p, 42p, upholstered pad 40u, 42u, and the elastomeric member 52, with its support plates 54 and 56, of each back support 40, 42 form a back support sub-assembly. The brackets 60 are assembled to the back support mounting members 20r and 20l as part of the assembly of the frame (back support mounting members 20r and 20l and cross members 22) of the seat back assembly 16. Each back support subassembly is then assembled to the brackets 50 and secured by the screws 58. The covers 40c, 42c are then installed and secured in any suitable manner on the upper back support 42 and lower back support 40.

Figure 8:
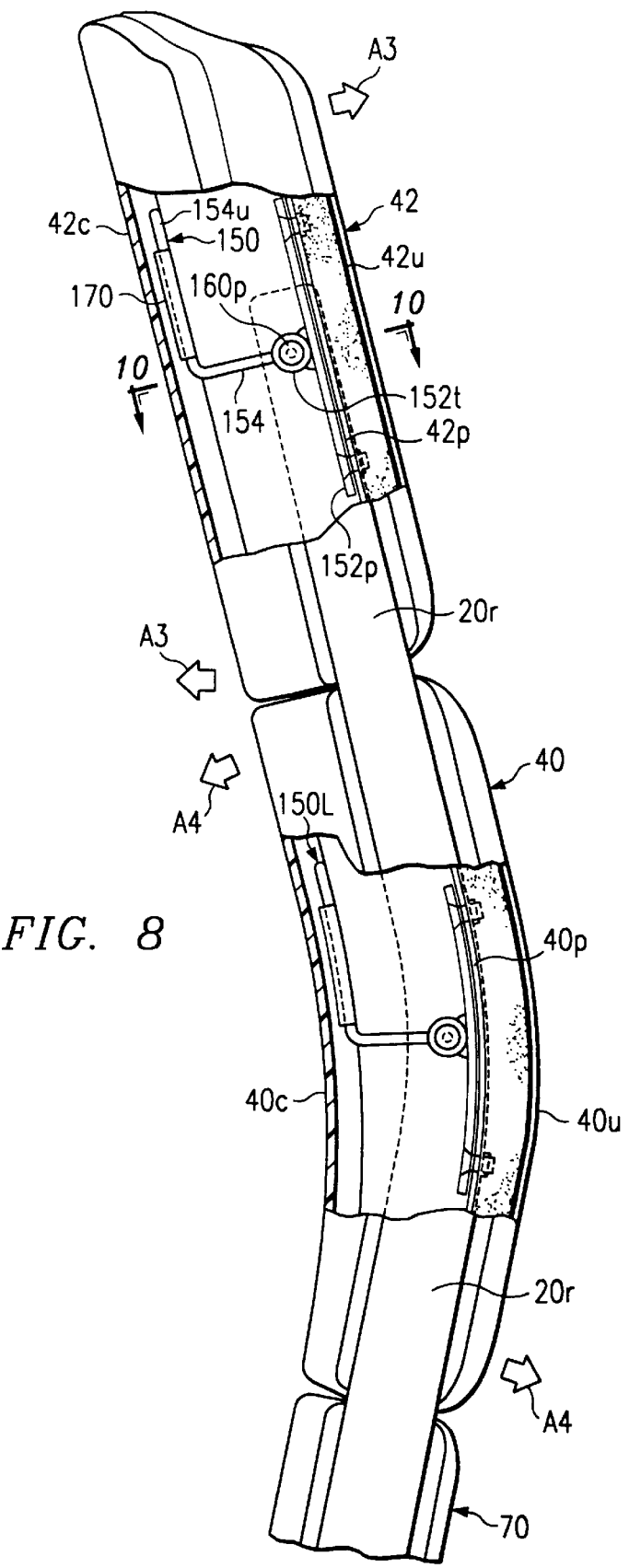
FIG. 8—a partial, generally schematic side cross-sectional view, showing a modified pivot mount for the back support.
Figure 11:
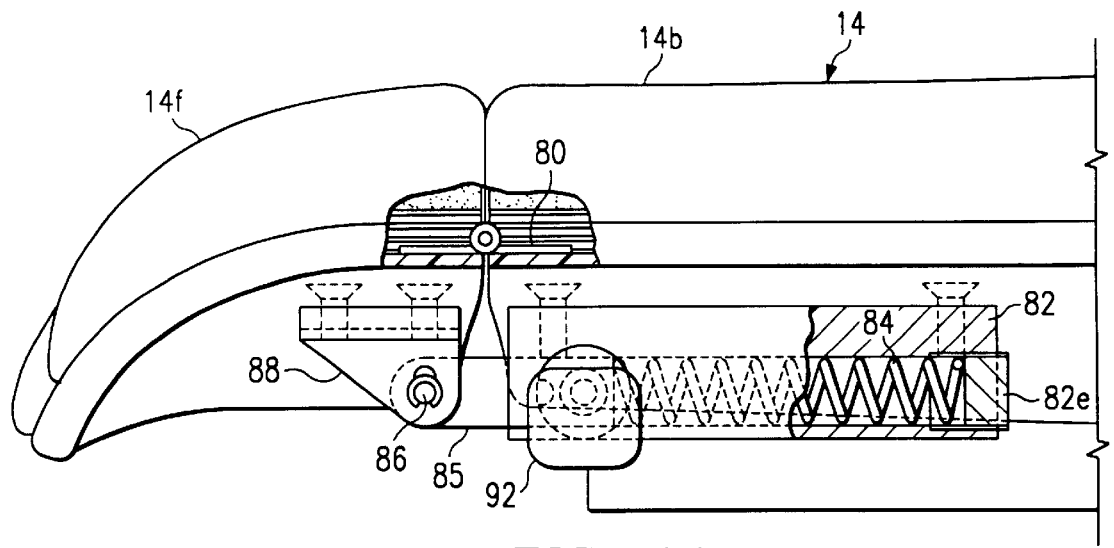
FIG. 11—a detail side elevational view of the front portion of the seat, portions being broken away.
Figure 12:
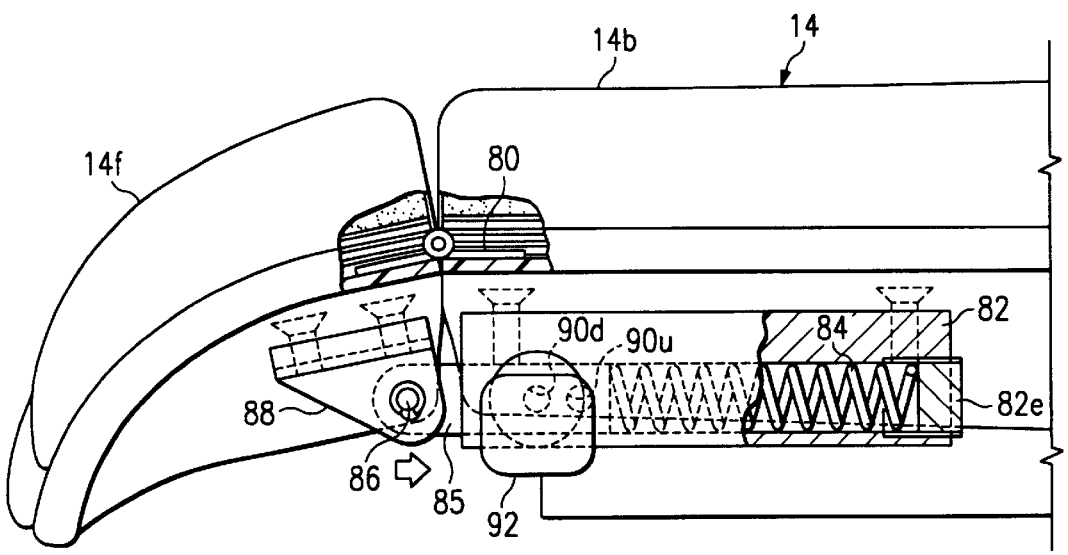
FIG. 12—the same view as FIG. 11, but showing a different position.
Figure 13:
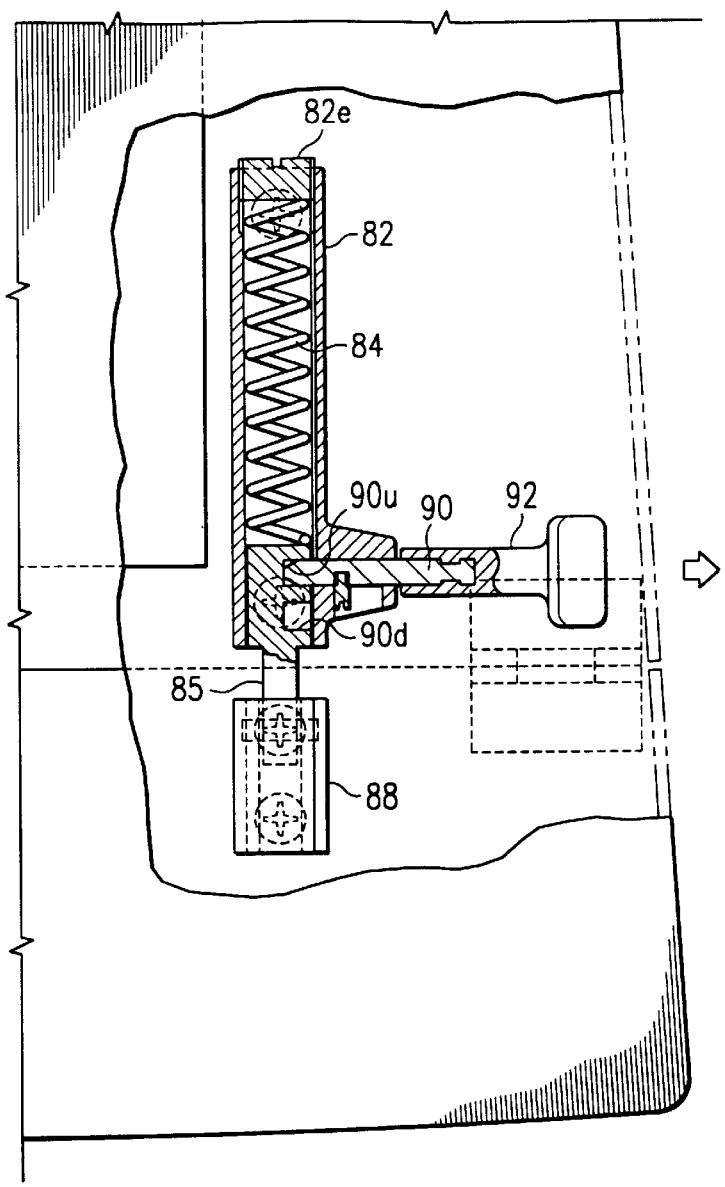
FIG. 13—a detail top plan view of a front corner portion of the seat, portions being broken away.
Figure 14:
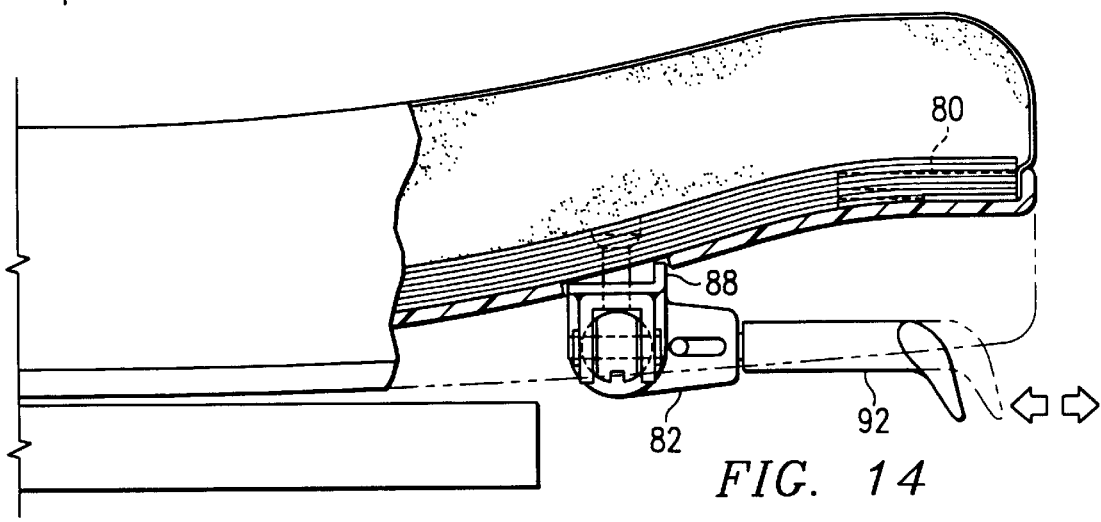
FIG. 14—a front elevational view of a part of the seat, a portion being broken away.
Figure 15:
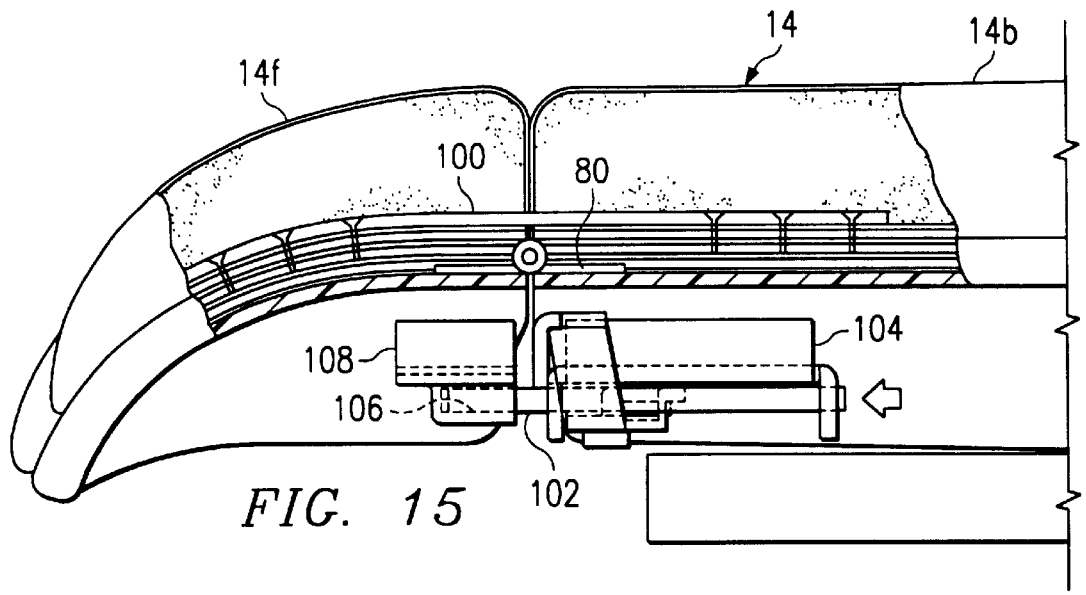
FIG. 15—a detail side elevational view of the front portion of the seat, portions being broken away and a modified support and latch unit being shown.

Resilient mount units of other constructions, such as the resilient mount unit 150 shown in FIGS. 8 to 10, may be used in a chair embodying the present invention to mount the back supports 40, 42 on the back support mounting members 20r, 20l. The unit 150 of the upper back support 42 includes at each side a bracket 152, consisting of a plate 152p and a tube 152t welded to the plate. The plate is fastened by screws to the pan 42p of the back support 42. The tube 152t is rotatably received on a pivot pin 60p that is welded to the back support mounting member (e.g., 20r). A bent end portion 154e of a torsion rod 154 is received in a spring coupling fitting 156. The bent portion 154e passes obliquely to the axis of the coupling fitting 156 through a slot 156s and is thereby affixed to the coupling tube 156 against rotation. The coupling fitting 156 is coupled against rotation to the pivot pin 160p by a rib and slot coupling 158 (FIG. 10). Thus, the bent end 154e of the torsion rod 154 is fixed against rotation relative to the pivot pin 60p.

The torsion rod 154 extends across the entire width of the back support 42. The other end of the torsion rod 154 (not shown) is linked to the other back support mounting member 20l. A "U" bend 154u in the center of the torsion rod 154 is clamped to the pan 42p by a clamp 170. In the relaxed state of the torsion rod 154, the back support is held in neutral position. When a person sitting in the chair changes his sitting posture such as to apply a force to the back support 42 tending to tilt it in either direction from the neutral position (see arrows A3), the U bend 154u is rotated, thus placing the torsion rod under load. The energy stored in the torsion rod returns the back support to the neutral position whenever no force tending to pivot it about the axis of the pivot pin 160p is applied to it.

The mount unit 150L for the lower back support 40 is the same as the mount unit 150 for the upper back support 42 except for size and shape.

Figure 3:
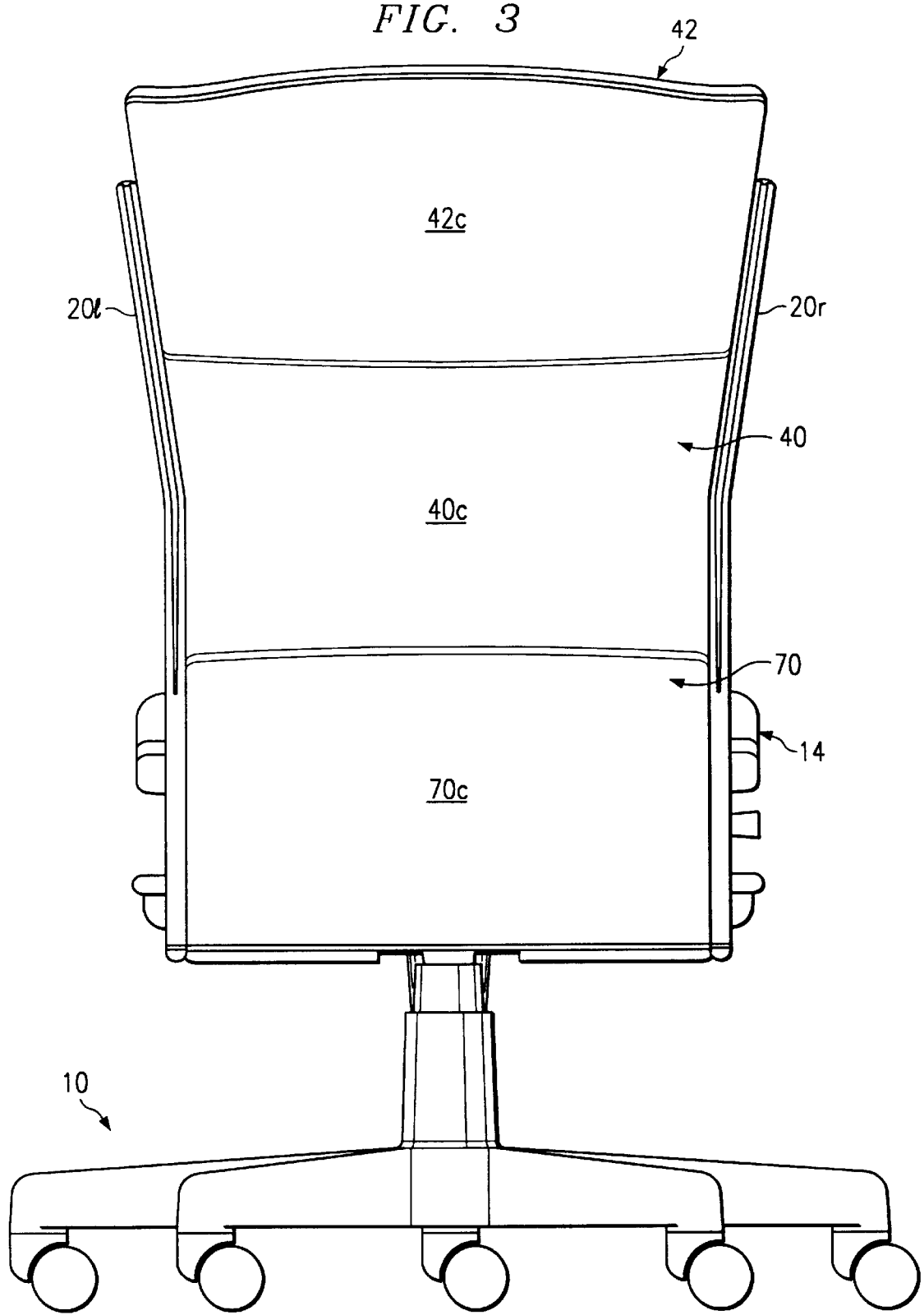
FIG. 3—a rear elevational view.

The space between the lower portions of the back support mounting members 20r and 20l and below the lower back support 40 is filled by a lower back panel 70, which includes a pan 70p, a rear cover 70c and upholstered padding 70u. The lower back panel 70 conceals the rear aspect of the mounting unit and the cross members 24 that connect the back support mounting members 20r and 20l and imparts a handsome appearance to the rear aspect of the chair (see FIG. 3). The lower back panel 70 also fills what would otherwise be a gap between the lower edge of the lower back support 40 and the seat bottom 14 (see FIG. 2).

Figure 4:
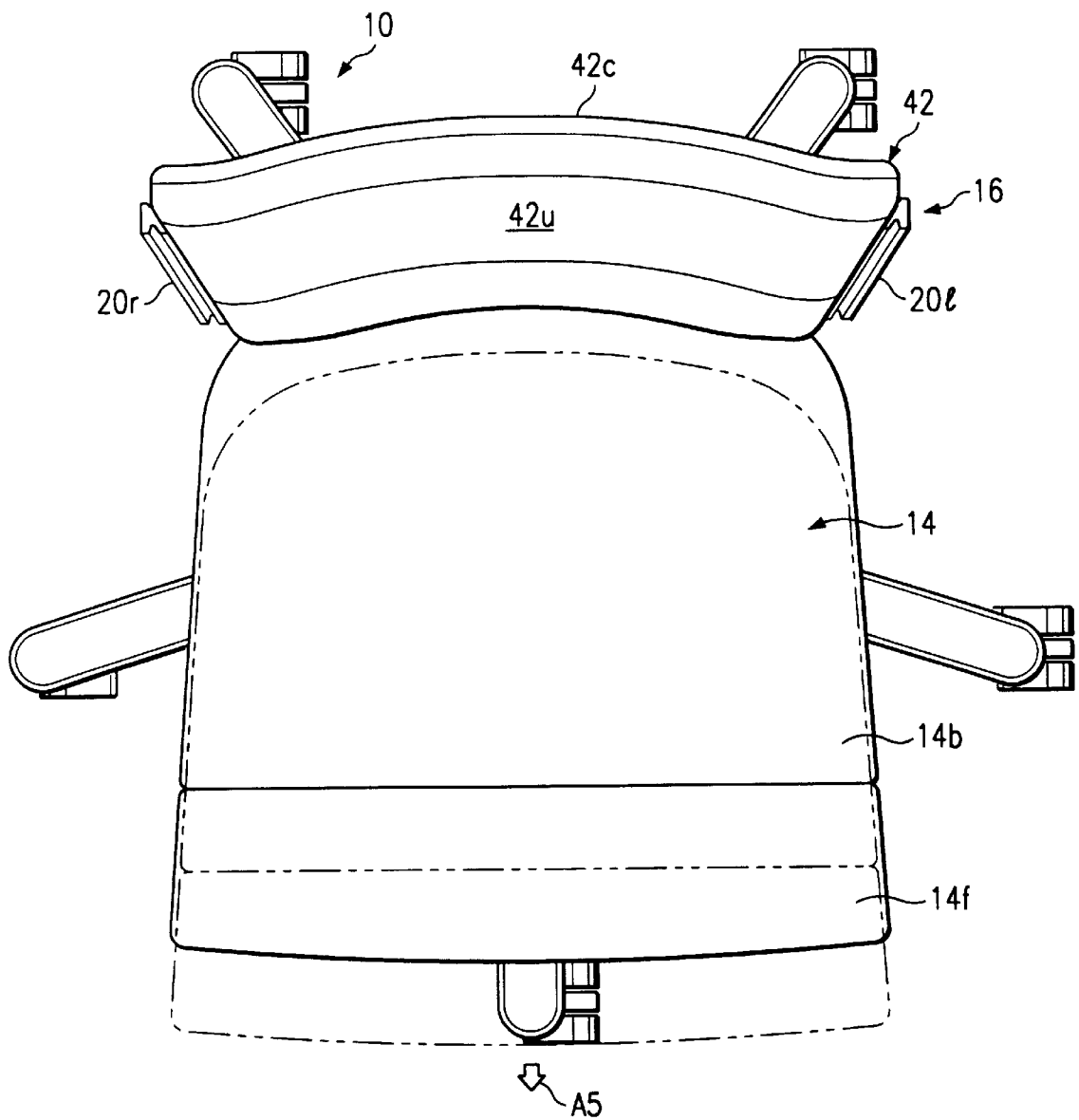
FIG. 4—a top plan view.

As shown in, for example, FIGS. 1 and 4, the seat bottom 14 includes a main body portion 14b and a tilting front portion 14f, which is attached to the front edge of the body portion to articulate downwardly, as indicated by the arrows A5 and the phantom lines in FIG. 1. The tilting front portion 14f is normally held resiliently in the position shown in solid lines by a resilient mount arrangement (examples described below). The tilting front portion 14f tilts down when the forward parts of the undersides of the user's thighs apply a force to it, thus limiting the pressure on the undersides of the user's thighs to the extent of the resilient force exerted by the mount arrangement. A seat latch (examples described below) may be included to hold the tilting seat portion in the normal "up" position, or the tilted down position, or both.

In one mount arrangement, as shown in FIGS. 11 to 14, a pair of hinges 80, one near each side edge of the seat bottom 14, are affixed to the structural pans of the main seat bottom 14b and the front seat bottom 14f. A spring housing 82 affixed to the underside of the pan of the main seat bottom receives a compression coil spring 84, which is compressed under a predetermined load between an end closure 82e of the housing 82 and a link 85, a rear portion of which is slidably received in the housing 82. The link 85 is coupled by a pin 86 to a slot cam fitting 88 affixed to the underside of the pan of the front seat bottom 14f. The spring 84, acting through the link 85 and fitting 88, biases the front seat part to an "up" position but yields when the spring force is exceeded so that the front seat bottom can tilt down and relieve the pressure on the underside of the thighs of a person sitting in the chair.

Some users may find the tilting movement of the front seat bottom disconcerting. If so, they may engage a latch pin 90 in either one of two latch holes 90u and 90d in the link 85 by pushing in an operating handle 92 (see FIG. 13). In the position shown in FIG. 13, the front seat bottom 14f is latched in the "up" position. When the pin 90 is located in the hole 90d, the front seat bottom is latched in the "down" position. When the pin 90 is retracted, the front seat bottom tilts up and down, depending on the load exerted on it by the user's thighs.

Figure 16:
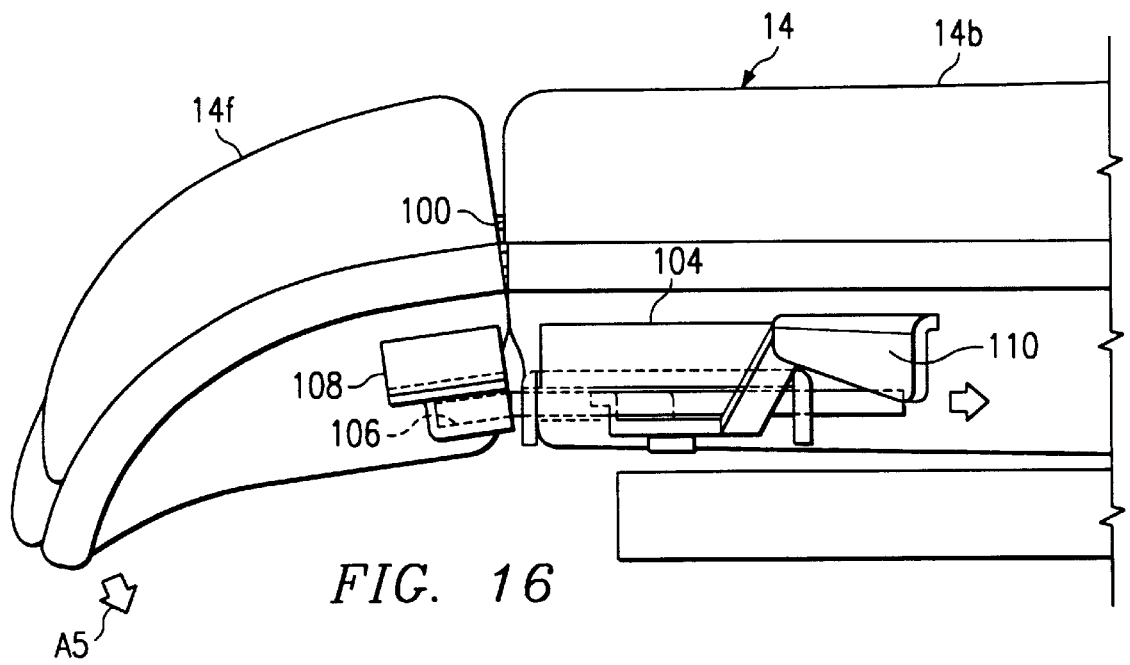
FIG. 16—the same view as FIG. 15, but showing a different position.
Figure 17:
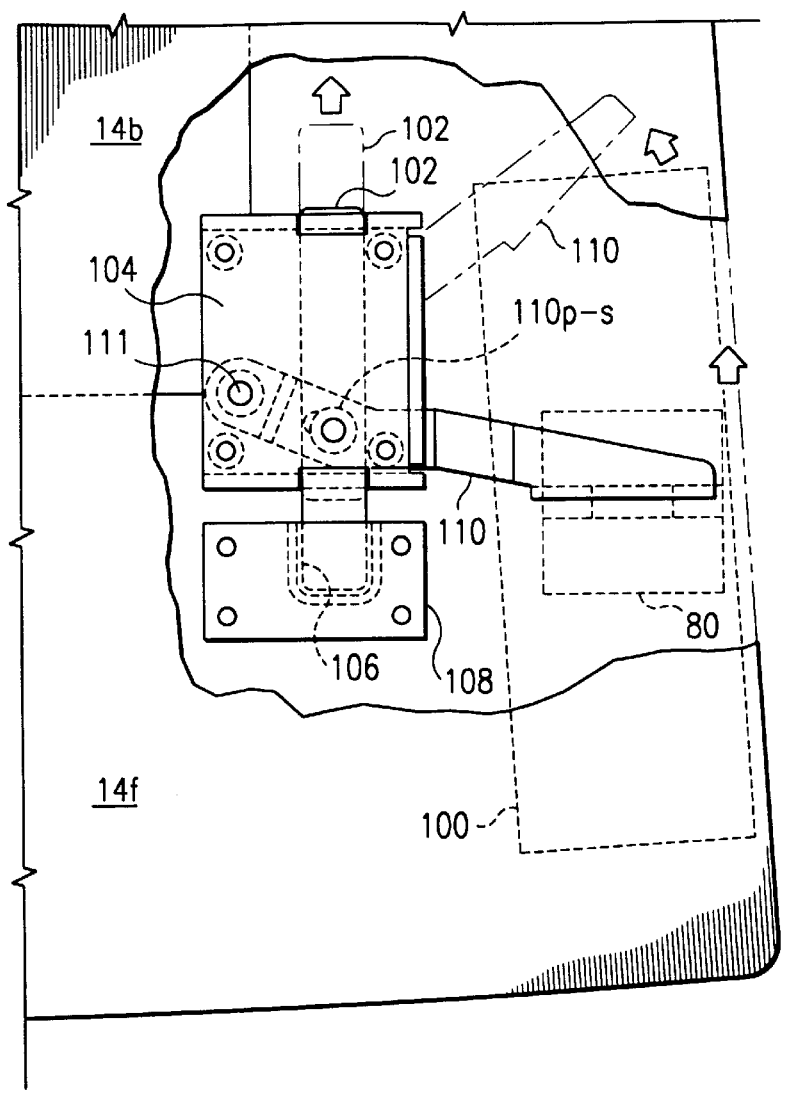
FIG. 17—a detail top plan view of a front corner portion of the seat of FIG. 15, portions being broken away.
Figure 18:
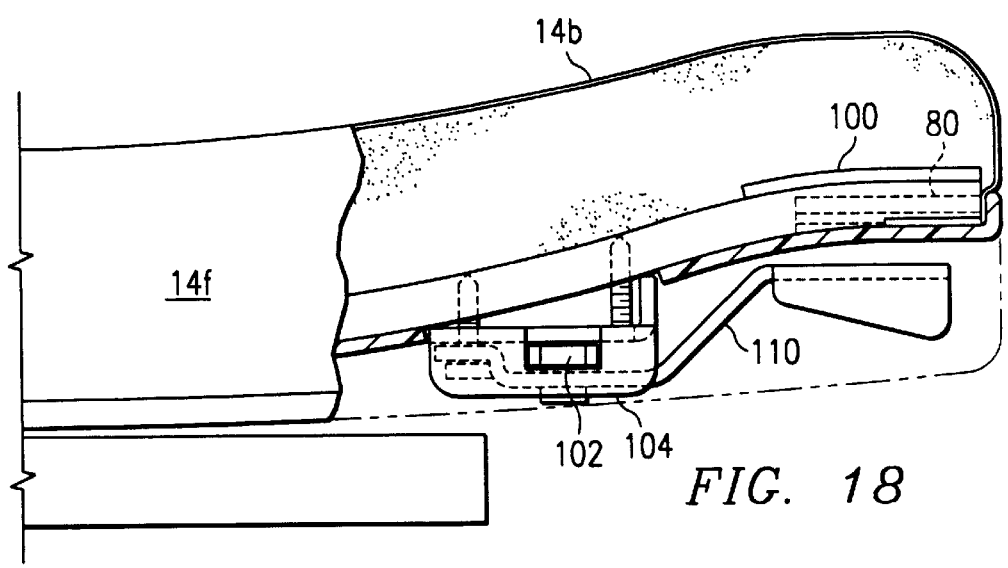
FIG. 18—a front elevational view of a part of the seat of FIGS. 15 to 17, a portion being broken away.

Another mount arrangement, as shown in FIGS. 15 to 18, uses elastic bands 100 near each side of the seat bottom to bias the front seat bottom 14f to the up position. The bands 100 are fastened with preloads by tacks or screws to molded plywood bases of the main seat bottom 14b and front seat bottom 14f, leaving a length of the bands 100 clear between the closest fasteners to allow stretching of the bands sufficient to accommodate the desired amount of downward tilting of the front seat bottom. A latch bar 102 slidably mounted on a carrier 104 affixed to the underside of the main seat bottom 14b is engageable in a socket 106 of a latch bar receiver 108 affixed to the underside of the front seat bottom. An easily accessible operating lever 110 linked to the latch bar by a pin and cam slot 110 p–s (FIG. 17) and pivotally mounted on the carrier 104 by a pivot pin 111 facilitates movement of the latch bar 102 between the latched position (FIG. 15), in which the front seat bottom cannot tilt down, and the unlatched position (FIG. 16).

Figure 19:
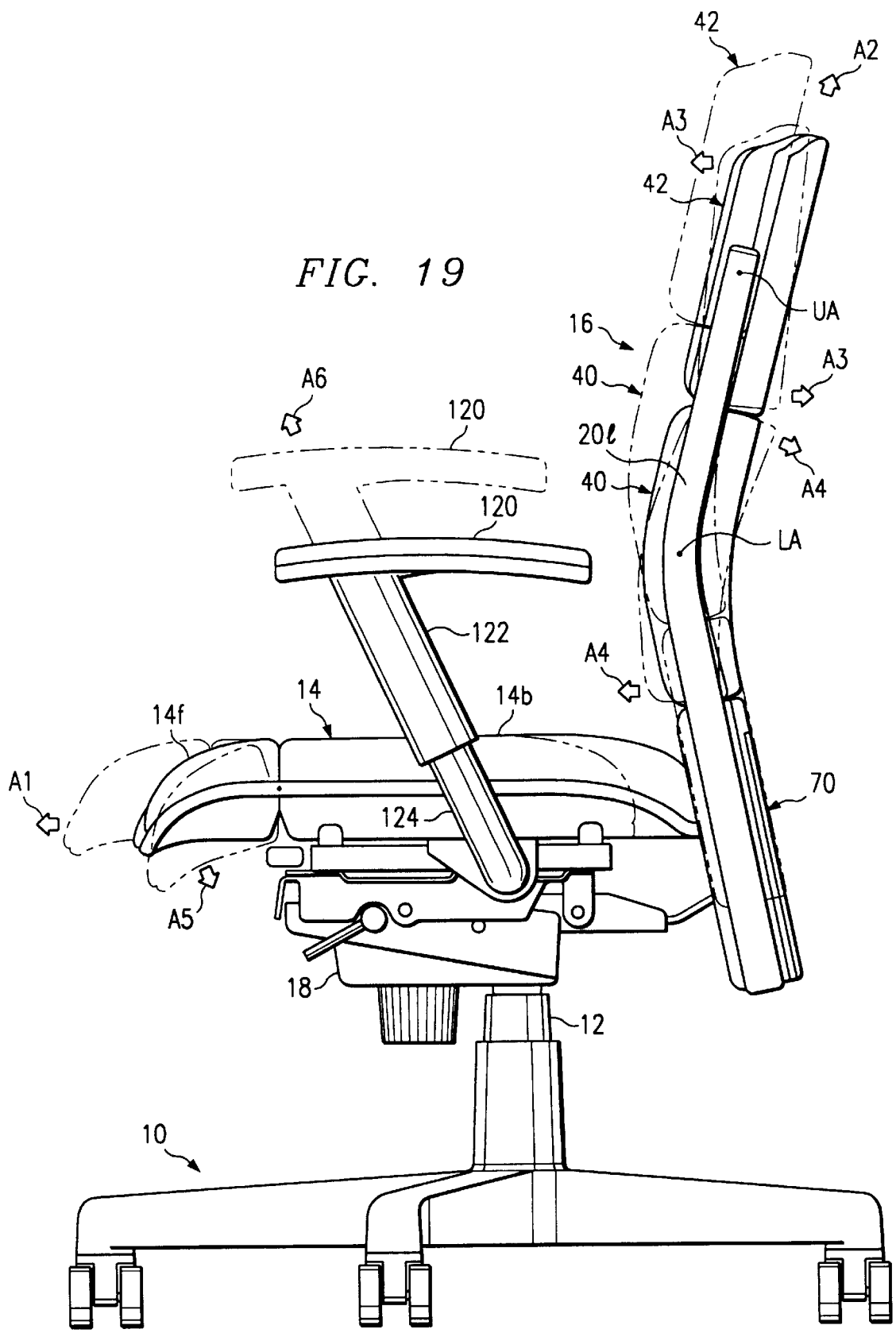
FIG. 19—a side elevational view, showing arms attached to the embodiment.
Figure 20:
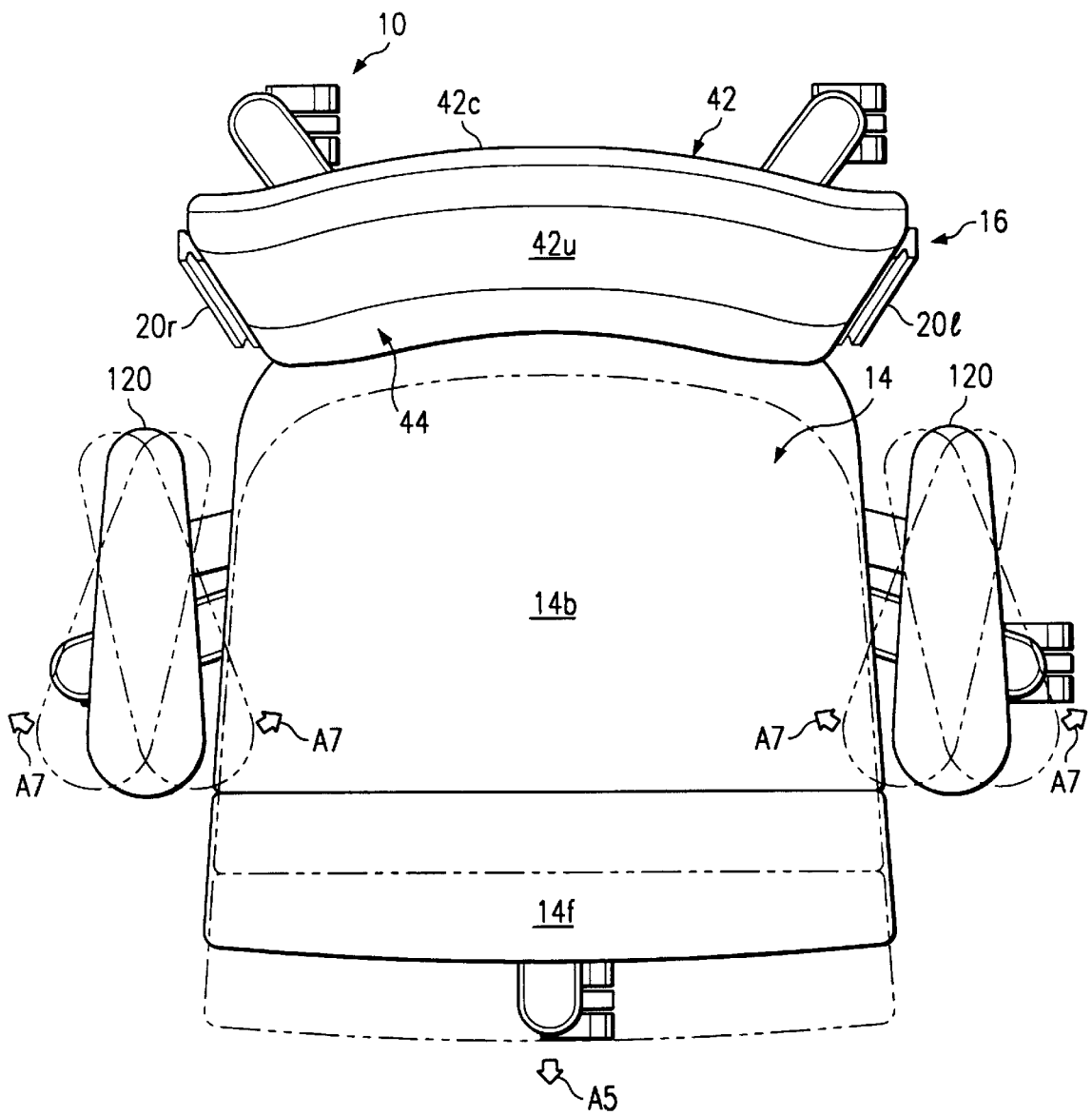
FIG. 20—a top plan view of the embodiment with the arms added.
Figure 21:
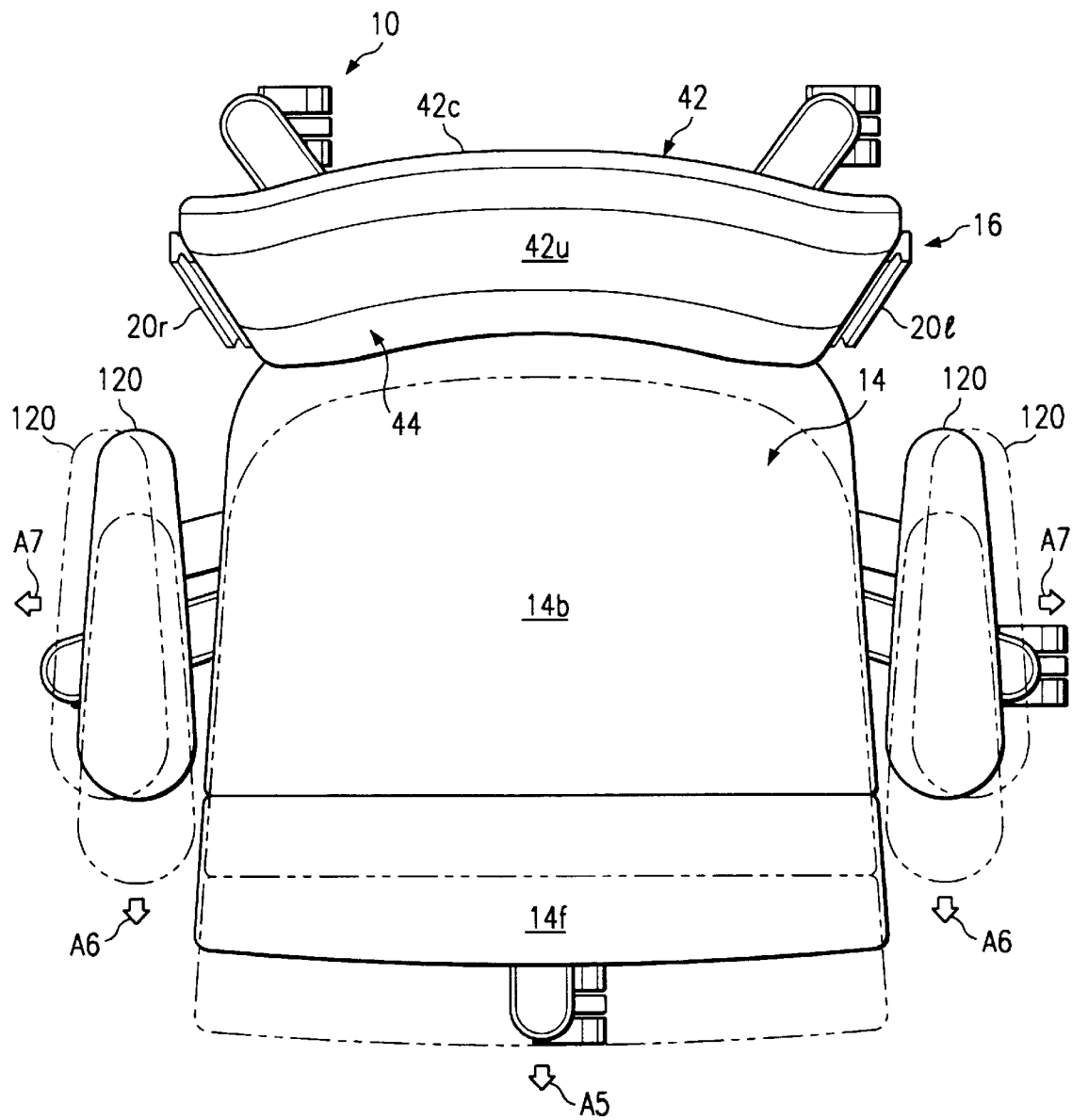
FIG. 21—the same view as FIG. 20, showing other adjustments of the arm rests.

Arms 120 of any suitable design can, if desired, be affixed to the seat-mounting mechanism 18 or the underside of the seat bottom 14, as shown in FIGS. 19 to 21.

Figure 22:
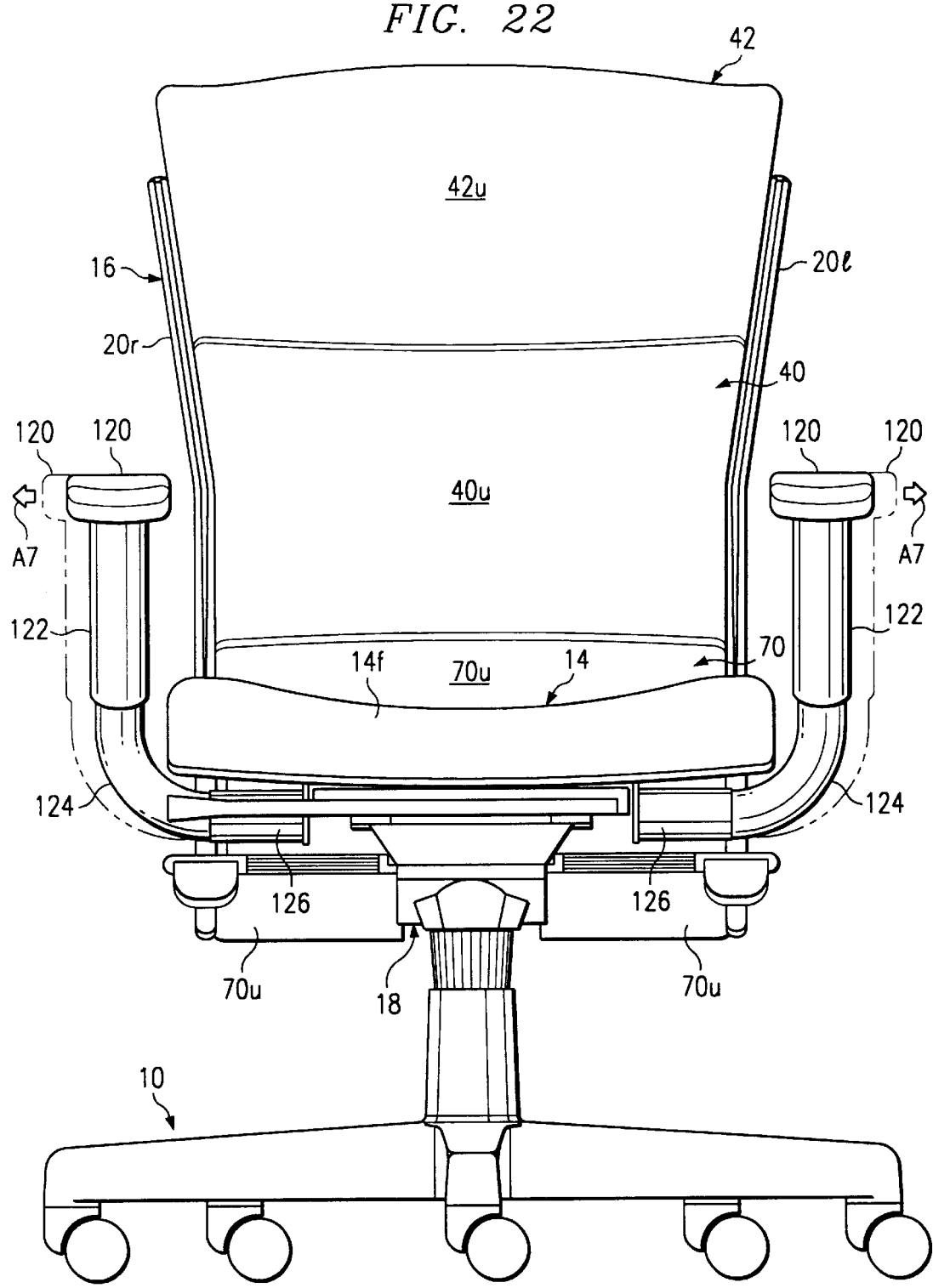
FIG. 22—a front elevational view of the embodiment with arms added.

Telescoping arrangements of arm support tubes 122, 124 and 126 and suitable locking devices (not shown) between the telescoping tubes enable adjustments of the heights and fore-aft positions of the arms (arrow AG, FIG. 19), angles of the arms to the fore-aft centerline (arrows A7, FIG. 20), and lateral spacing of the arms (arrows A7, FIGS. 21 and 22) to fit the chair optimally to the size of the user.

What is claimed is:

1. A chair comprising
   a frame having a pair of spaced-apart stationary back support mounting members,
   a lower back support adapted to support the dorsal portion of the back of a person seated on the chair,
   lower resilient mount units mounting the lower back support directly on the back support mounting members for pivotal movement about a horizontal pivot axis located at substantially the vertical center of the lower back support and biasing the lower back support to a predetermined position,
   an upper back support adapted to support the upper portion of the back of a person seated on the chair, and
   upper resilient mount units mounting the upper back support directly on the back support mounting members for pivotal movement about a horizontal pivot axis located at substantially the vertical center of the upper back support and biasing the upper back support to a predetermined position,
   the back supports being configured to provide support for the user's back throughout the region from the sacrum to just above the shoulders.

2. The chair according to claim 1, wherein each of the resilient mount units includes an elastomeric body affixed to and interposed functionally between the back support and the back support mounting member.

3. The chair according to claim 1, wherein the back support mounting members are located laterally abreast of the back supports.

4. The chair according to claim 1, wherein each back support includes a structural pan and upholstered padding carried by the pan.

5. The chair according to claim 1, wherein each of the back supports is generally rectangular and the side edges of each of the back supports are closely adjacent to the back support mounting members.

6. The chair according to claim 1, wherein the upper edge of the lower back support is closely adjacent to the lower edge of the upper back support.

7. The chair according to claim 1, wherein each of the lower back support and the upper back support is transversely curved and presents a transversely concave front surface that corresponds in shape generally to the transverse curvature of the anatomical back of a person.

8. The chair according to claim 7, wherein the lower back support is vertically curved and presents a vertically curved convex surface that corresponds in shape generally to the vertical curvature of the dorsal portion of the anatomical back of a person.

9. The chair according to claim 1, and further comprising a base having a seat mount that includes a back support bracket, and wherein the back support mounting members are joined by a transverse framework that is supported by the back support bracket for adjustment of the height of the back support mounting members.

10. The chair according to claim 1, and further comprising a seat bottom unit having a main part and a front part, the rear edge of the front part being coupled to the front edge of the main part for articulation of the front part relative to the main part between a resiliently restrained up position and a tilted down position.

11. The chair according to claim 10, and further comprising a latch for affixing the front part in the up position.

12. The chair according to claim 10, and further comprising a latch for affixing the front part in the down position.

13. The chair according to claim 10, and further comprising a base having a seat mount and wherein the seat bottom unit is mounted on the seat mount for adjustment forwardly and rearwardly relative to the seat mount.

14. The chair according to claim 1, wherein the back support mounting members are located laterally abreast of the back supports, each of the back supports is generally rectangular, the side edges of each of the back supports are closely adjacent to the back support mounting members, and the upper edge of the lower back support is closely adjacent to the lower edge of the upper back support.

15. The chair according to claim 14, wherein each back support includes a structural pan and upholstered padding carried by the pan.

16. The chair according to claim 15, wherein each of the resilient mount units includes an elastomeric body affixed to the structural pan of the back support and the back support mounting member.

17. The chair according to claim 16, wherein each of the resilient mount units further includes a first support plate affixed to one side of the elastomeric member and to the structural pan, a second support plate affixed to the other side of the elastomeric member, a mounting bracket affixed to the back support mounting members, and a screw affixing the mounting bracket to the second support plate.

18. The chair according to claim 17, wherein the structural pan includes a cavity receiving the first support plate and a portion of the elastomeric member.

19. The chair according to claim 18, wherein each back support mounting member is tubular and has side walls, and the mounting bracket includes a mounting post that passes through a hole in one side wall of the back support mounting member and is joined to the opposite side wall of the back support mounting member by a weldment at a weld site that includes a hole in the opposite side wall.

* * * * *

UNITED STATES PATENT AND TRADEMARK OFFICE
CERTIFICATE OF CORRECTION

| | |
|---|---|
| PATENT NO. | : 6,478,379 B1 |
| DATED | : November 12, 2002 |
| INVENTOR(S) | : Ambasz |

It is certified that error appears in the above-identified patent and that said Letters Patent is hereby corrected as shown below:

<u>Title page,</u>
Item [56], References Cited, U.S. PATENT DOCUMENTS, insert:
-- 3,057,660    10/1962    Schneider --.

<u>Column 5,</u>
Line 51, "20*ls*" should read -- 20*l* --

Signed and Sealed this

Twenty-sixth Day of August, 2003

JAMES E. ROGAN
*Director of the United States Patent and Trademark Office*